(12) United States Patent
Wulfsohn et al.

(10) Patent No.: US 8,425,409 B2
(45) Date of Patent: Apr. 23, 2013

(54) LARYNGOSCOPE

(75) Inventors: Norman Wulfsohn, San Antonio, TX (US); Olivier Picquenot, San Antonio, TX (US)

(73) Assignee: VM Specialty, Inc., San Antonio, TX (US)

( * ) Notice: Subject to any disclaimer, the term of this patent is extended or adjusted under 35 U.S.C. 154(b) by 1058 days.

(21) Appl. No.: 11/925,302

(22) Filed: Oct. 26, 2007

(65) Prior Publication Data
US 2009/0114217 A1     May 7, 2009

(51) Int. Cl.
*A61B 1/267*     (2006.01)
(52) U.S. Cl.
USPC .......................................................... 600/185
(58) Field of Classification Search .................. 600/185, 600/188, 191, 199
See application file for complete search history.

(56) References Cited

U.S. PATENT DOCUMENTS 6,217,514 B1 *   4/2001   Gruen et al. .................. 600/185
7,878,973 B2 *   2/2011   Yee et al. ...................... 600/199

* cited by examiner

*Primary Examiner* — Anu Ramana
(74) *Attorney, Agent, or Firm* — David G. Henry; Katarzyna Brozynski

(57) ABSTRACT

An improved Laryngoscope having a decreased angular projection between a blade portion and a handle portion of approximately 70° with a substantially continually curved transition portion bridging the blade and handle portions and providing a teeth-protecting structure, when compared to conventional scopes. At a distal end of the blade portion is a tissue elevation lobe which is used to depress tissues and structures which otherwise would obstruct visualization of vocal chords during an intubation, giving its user added tissue control with minimized handle manipulation being required. The scope is constructed of light-transmitting plastic and includes a step-down transition margin near the tissue elevation lobe at which margin a portion of light which is projected into the scope at or near the handle end projects from the scope to illuminate the intubation site.

2 Claims, 1 Drawing Sheet

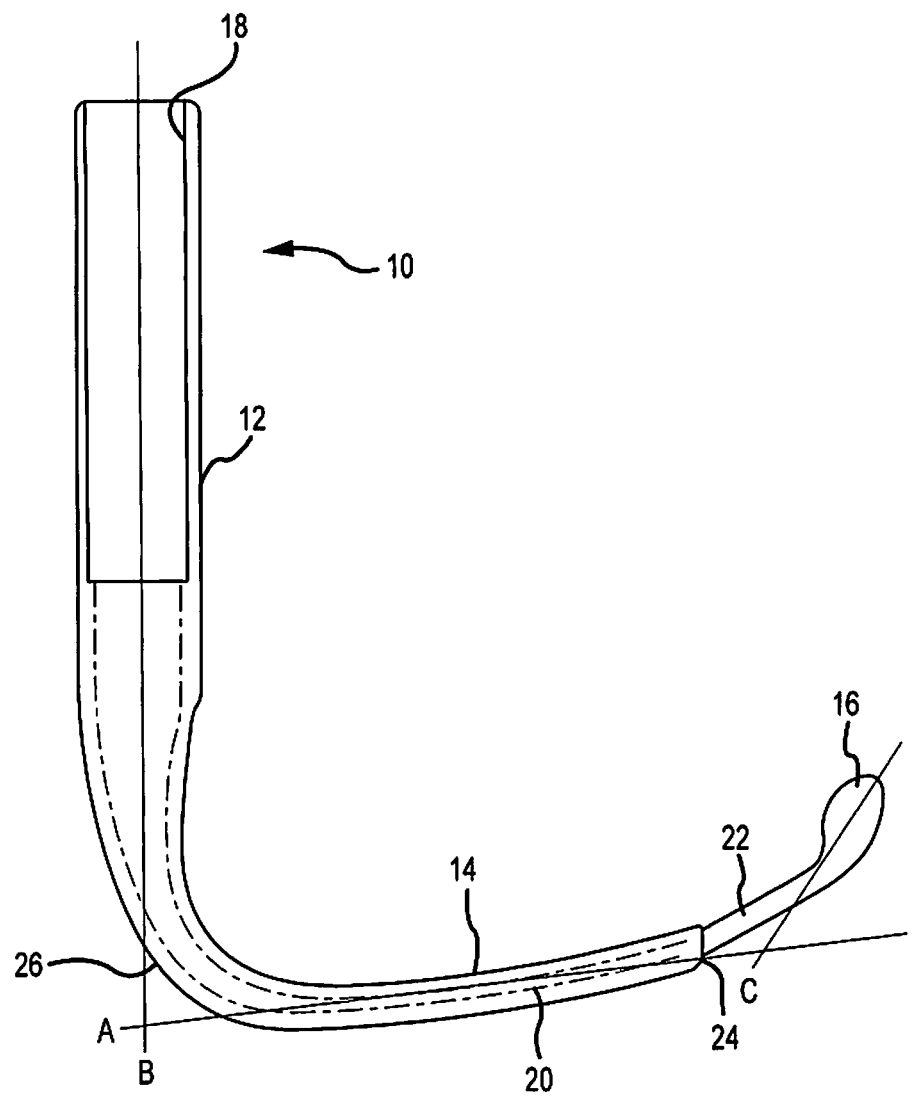

LARYNGOSCOPE

BACKGROUND OF THE INVENTION

1. Field of the Invention

Applicant's invention relates to endoscopy and to instruments and methodologies that are useful in intubation procedures.

2. Background Information

Endotracheal intubation is the process by which a tube is inserted into the trachea of an individual who requires assistance in breathing. The need for intubation often arises from a cardiac and/or pulmonary arrest, or from trauma when the patient is unable to breath without outside intervention. Alternatively, elective intubation may be involved in preparing a patient for surgery under general anesthesia when the capacity for independent breathing may be interrupted. Over 10 million intubations are performed annually in the United States in approximately 6100 hospitals and 4000 ambulatory patient care facilities.

Intubation is a standard procedure for obtaining an artificial airway, but it can be difficult for the medical professional, and potentially dangerous for the patient. Properly negotiating the anatomy of the oropharynx and the larynx to ultimately place a tube in the trachea requires that the tube pass through the vocal cords, which are not always visible at the time of intubation. Thus intubation is often a partially blind procedure that relies on imperfect and indirect methods for confirming proper tube placement.

A Laryngoscope is an instrument designed and taught to be held with the left hand during intubation. It is used to divert the patient's tongue, epiglottis and other structures, and thereby enabling visualization of the vocal cords. However, often even with the Laryngoscope in an optimal position, the vocal cords cannot be visualized due to a variety of reasons, including the presence of a small mouth opening, an inability to optimally position the head and/or neck due to trauma or other reasons, or to an anterior position of the larynx. With any of these or similar conditions, placement of the tube becomes a partially blind procedure.

The most critical phase of intubation occurs when the tube is seen passing between the vocal cords and into the trachea. Without actually viewing the tube passing between the vocal cords and into the trachea, an intubation becomes more difficult or even impossible. Therefore, absolute certainty of the proper placement of the tube in the trachea is a fundamental requirement of every intubation.

If the vocal cords are visualized and the tube is seen passing through the vocal cords and into the trachea, post-intubation methods for verifying proper tube placement are still required to assure that the tube is in proper position within the trachea—2 cm above the tracheal bifurcation, or carina. The best confirmation method is to directly see the tube pass between the vocal cords and into the trachea, and the ideal time to know that this has occurred is during intubation itself. Properly securing the airway is the vital first step in patient resuscitation and in maintaining life support.

Methods for confirming proper tube placement, and thereby excluding an improper esophageal intubation (which precludes adequate oxygen delivery and carbon dioxide removal in the patient), an improper bronchial intubation (which blocks gas flow to the opposite lung), or improperly placed endotracheal intubation, are not always reliable because they are not sensitive or specific enough to provide absolute certainty of proper tube placement. Even the most reliable methods currently used for verifying properly placed tracheal intubation are indirect, take place after intubation, are undesirably time consuming, unnecessarily expensive, and can be associated with undesirable effects (e.g., radiation exposure in the case of chest x-ray confirmation).

The most commonly employed indicators for proper placement of a tube involves:

1) Auscultation, i.e., listening to the chest for breath sounds when the patient is ventilated. Such apparent indication of proper tube placement has, however, been reported in cases that ultimately turned out to involve esophageal intubations.
2) Pulse oximetry. An unrecognized or delayed recognition of an esophageal intubation will only eventually cause a decrease in oxygen saturation—several minutes may elapse before this occurs. In one study, detection of an esophageal intubation required 5 or more minutes in 97% of the cases.
3) Capnography detects carbon dioxide emission from the tube, which indicates that the tube is in communication with the patient's lungs and is serving as a conduit for exhausting the carbon dioxide of respiration. This method involves the expense of a disposable carbon dioxide sensor and is susceptible to both false positive and false negative results under certain circumstances that relate to the patient's gastric state and/or cardiac function at the time of intubation.
4) Chest radiography. X-ray verification involves radiation exposure, which should be avoided when non-radiation methods are equally or more efficacious. Besides, radiographic verification of proper tube placement is time consuming, adds expense and is not absolutely reliable. Also, since in surgical patients the x-ray is taken after surgery in the post-anesthesia care unit or in the intensive care unit, determination of an improper endotracheal intubation can be delayed.

In light of the limitations of indirect, post-intubation indication of proper tube placement, it is best to insure that one achieves visualization of the vocal cords for insuring certain passage of the endotracheal tube therethrough.

Presently, quite elaborate means are employed to achieve endotracheal tube passage visualization. As will be explained in more detail later, this is the result of those in the art failing to recognize that changes to existing Laryngoscope designs can more effectively, efficiently and inexpensively solve the problem, than can the to-be-described, elaborate methods.

An endoscope presents an image of a remote site within the body to a viewer outside the body. This can be achieved using a number of methods, including direct imaging of the site through conventional optical elements in a rigid array, indirect relay of the image through a flexible image conduit using conventional optics at either end, or by forming an image on an electronic imaging device proximal to the site and displayed on a monitor, or other viewing device.

Fiberoptic-based endoscopes are used by some to visualize proper endotracheal tube placement. No existing endoscope allows for simultaneous adjustment to the airway anatomy during an intubation with continuous visual confirmation of proper tube insertion. Two fiberoptic-aided intubation methods are presently available: 1) the "tube-first" approach, and 2) the "endoscope-first" approach.

In the tube-first approach to fiberoptic intubation, an intubating airway (a plastic device that is placed temporarily in the patient's mouth [oropharynx] to guide a tube generally toward its intended target) is placed in the oropharynx, and a tube is then inserted into the passageway of the intubating airway. While a second person supports the tube, which is now held in position by the intubating airway, an adult bronchoscope is inserted into the tube and advanced (using both hands) through the tube, through the vocal cords, and into the trachea. Using the endoscope insertion cord as a guide wire, the second person then blindly advances the tube over the endoscope and hopefully into the trachea. The bronchoscope, which served the purpose of a passive guide wire, is then withdrawn while holding the tube in place, after checking for proper tube placement.

The tube-first approach to fiberoptic intubation using presently available equipment has limitations. The stiffer tube can easily displace the thin, pliable insertion cord of currently available endoscopes. Thus, the tube may not follow the intended path of the correctly-placed endoscope insertion cord into the trachea, but rather the tube may drag the insertion cord along a path along a path of least resistance into the esophagus.

An uncommon but difficult situation may arise as the endoscope is being advanced through the tube. As the distal tip of the endoscope nears the distal end of the tube, the endoscope tip may (and often does) pass through the Murphy's eye of the tube. The Murphy's eye, an opening in the side of the tube (or side port) 1 cm. from the tip, prevents complete occlusion of the tube if the opening becomes blocked. If the endoscope tip is unintentionally passed through the Murphy's eye during an intubation, withdrawing the tube may be impossible without injury to the patient. Maneuverability of the tube/endoscope complex is severely diminished. (As stated earlier, this Murphy's eye entanglement problem is rare; however, such problems would be non-existent with the proposed endoscope.)

In the endoscope-first approach, the medical professional first attempts to direct the endoscope, with a tube pre-loaded back on the most proximal portion of the endoscope insertion cord, into the trachea, after which the tube is, as described before, advanced over the endoscope, using the endoscope essentially as a guide wire, into the trachea. This approach reduces the likelihood of advancing the endoscope tip through the Murphy's eye, but retains the limitations of the endoscope to act as a guide wire. The existing endoscope insertion cords are often too flexible to reliably guide a tube to an intended position in the trachea. This is true, in part, because as the tube is advanced over the endoscope, the endoscope passively (and blindly to the operator) guides the advancing tube to its intended endotracheal position, often through unyielding airway anatomy that can, combined with the forces used to advance the tube, divert the tube away from the intended path with an overall force that is greater than the passive guide wire can resist.

There are other significant limitations of the current fiberoptic technology. For example, in both the tube-first approach and the phases of the endoscope-first approach, during which the tube is advanced over the endoscope, the distal margins of the tube may get caught on laryngeal anatomy and thus be incapable of being advanced into the trachea. Also, during any phase of an intubation where one attempts to advance a tube over an already-placed endoscope, there may be a tendency to pull the endoscope back from its proper position as the tube is advanced, thereby resulting in an esophageal intubation or other complications. This is true particularly because two practitioners are required for currently practiced fiberoptic intubation procedures, one of whom must be well trained and experienced in bronchoscopy. Perfect coordination between the two, or detecting the lack thereof in the often hectic environment of a difficult intubation is not always possible.

The need for two practitioners for fiberoptic intubation procedures arises, in part, from the fact that currently available endoscopes and tubes are not specifically designed to be used together. The length of presently available endoscopes far exceeds that of the tubes with which they may be used, making their operation more complex. They lack a stylet function which would be helpful in manipulating the endoscope and tube as one unit and ensuring that the endoscope, and the loaded tube, will follow a desired path shape that ends in the proper location within the trachea.

In lieu of such complex approaches to achieving visualization in difficult airway situations, the present invention is of an improved Laryngoscope which in the vast majority of cases will obviate the need for such approaches.

There are many advantages of the proposed, improved Laryngoscope. Medical professionals and patients would benefit from a single device that addresses the deficiencies of equipment currently used to perform intubation, and requires only using standard hand motions used by most practitioners who perform routine intubations in direct laryngoscopy. Another primary advantage is that such an improved instrument would substantially simplify intubation and significantly increase the probability that each intubation will proceed properly, swiftly, and safely.

The benefit of the Laryngoscope design set forth herein derives from its enhanced ability to facilitate vocal chord visualization. This, in turn, arises from subtle, but highly significant contours and relative orientations of portions of the instrument.

In contrast to present Laryngoscope designs, the proposed Laryngoscope, far better than existing such instruments, displaces tissues which otherwise in most cases obscures visualization of the vocal chords, provides a "mechanical advantage" with respect to such displacement relative to wrist movement by the person conducting the intubation, whereby no observable, additional effort is required, nor difficulty is involved in utilizing the instrument's beneficial features and produced results, and protects the patient's teeth from damage which would otherwise be likely through use of conventional Laryngoscopes in achieving, or even attempting to achieve similar results.

The Laryngoscope of the present inventors' design involves a lobe, or distal enlargement, at the instrument's insertion end terminus. The size, shape and orientation of this lobe, relative to the instrument's handle and blade portions, facilitates a lifting and displacement of a patient's tongue during the intubation in a way not previously attainable with existing instruments, and in particular with such ease as is typical for use of the instrument of the present invention. The contours and relative orientations of the instrument's blade and handle portions, combined with the distal lobe, renders its optima use with minimal effort for even the moderately trained professional, while protecting the patient's teeth from Laryngoscope damage.

SUMMARY OF THE INVENTION

It is an object of the present invention to provide an improved Laryngoscope for use in intubation procedures.

It is another object of the present invention to provide a design for an improved Laryngoscope, instruments according to such design affording easier, more reliable, and safer intubations, through novel structural features for manipulating tissues for improved visualization of a patient's vocal chords during an intubation.

It is another object of the present invention to provide a design for an improved Laryngoscope, instruments according to such design affording easier, more reliable, and safer intubations, in part, through inclusion of a novel distal lobe at the insertion end of the instrument for manipulating tissues for improved visualization of a patient's vocal chords during an intubation.

It is another object of the present invention to provide a design for an improved Laryngoscope, instruments according to such design affording easier, more reliable, and safer intubations, in part, through inclusion of a novel distal lobe at the insertion end of the instrument for manipulating tissues for improved visualization of a patient's vocal chords during an intubation, such distal lobe being sized and positioned relative to remaining portions of the instrument, to provide optimal soft tissue management during an intubation, with minimal effort and maximum patient safety.

It is another object of the present invention to provide an improved Laryngoscope for performing intubation procedures, which instrument significantly decreases the Intubation Difficulty Scale (IDS) score using the endoscope compared to standard intubation methods for difficult intubations. (The IDS is a quantitative scale of intubation difficulty used to compare the ease of intubations; the purpose of the scale to evaluate intubating conditions and techniques to determine the relative values of predictive factors on intubation difficulty and of the techniques used to decrease such difficulties.)

In satisfaction of these and related objectives, Applicant's present invention provides an improved Laryngoscope which includes a lobe, or distal enlargement, at the instrument's insertion end terminus. The size, shape and orientation of this lobe, relative to the instrument's handle and blade portions, facilitates a lifting and displacement of a patient's tongue during the intubation in a way not previously attainable with existing instruments, and in particular with such ease as is typical for use of the instrument of the present invention. The contours and relative orientations of the instrument's blade and handle portions, combined with the distal lobe, renders its optima use with minimal effort for even the moderately trained professional, while protecting the patient's teeth from Laryngoscope damage.

BRIEF DESCRIPTION OF THE DRAWINGS

FIG. 1 is a side elevational view of the improved Laryngoscope according to embodiments of the present disclosure.

DETAILED DESCRIPTION OF THE PREFERRED EMBODIMENT

Referring to FIG. 1, the proposed Laryngoscope of the present invention is identified generally by the reference numeral 10. Laryngoscope 10 includes a handle portion 12, a blade portion 14 and a tissue displacement lobe or enlargement ("lobe") 16.

The laryngoscope 10 of the preferred embodiment is constructed of a clear plastic material, such as LEXAN, for light transmission purposes, as will be discussed below. All discussions to follow, unless specifically otherwise indicated, will be of the preferred embodiment of the present invention. Features such as material of construction and features and characteristics other than those emphasized in the preceding sections, are more specific than the invention of its properly claimed, broadest scope, and are not to be "read into" the broadest claims.

The handle portion 12 of Laryngoscope 10 includes an axial recess 18 into which can be inserted a light source (not shown in the drawings). Such a light source is provided, if at all, for transmitting light through the instrument itself to light the patient's physiology adjacent to the instrument's distal terminus. A high luminous, battery operated LED light source is envisioned as being ideal for the present application, such as one which might include a LUXEON LED. While alternative light sources are acceptable, use of such an LED light source with independent power will facilitate the instrument's use in the field, such as by EMS technicians or military medics in non-hospital environments.

Blade portion 14 of Laryngoscope 10 includes two principle sub-portions: the blade segment 20 and the lobe extension 22 at the distal end of which appears lobe 16. The transition between blade segment 20 and lobe extension 22 includes a light window 24. Light window 24 is formed through inclusion of a substantially angular step-down between the distal end of blade arch 20 and the proximal end of lobe extension 22, such being formed to include a substantially planer surface which lies somewhat close to an orthogonal orientation relative to the over-all lengthwise orientation of blade portion 14 of Laryngoscope 10. Light window 24, formed somewhat as generally described, provides an exit point for a portion of light which originates at the previously described light source and, by exiting through light window 24, illuminates anything adjacent the distal end of Laryngoscope 10.

The relative orientations of the identified portions of Laryngoscope 10, as well as the transitions therebetween are important to its beneficial use. First, a Line A (a "blade portion axis") which includes each terminus of blade segment 20 will form an approximately 70° angle relative to a Line B (a "handle portion axis") which extents through the longitudinal axis of handle portion 12. Intervening the handle portion 12 and blade portion 14 is a transition portion 26. Transition portion 26 of Laryngoscope 10 exhibits an arcuate configuration, with the arc lying substantially in the same plane as the handle portion 12 and blade portion 14. The combination of these features provides optimal utility with respect to manipulating the instrument to maximum beneficial effect, while protecting the patient's teeth from damage which can ordinarily attend the use of Laryngoscopes which include substantially angular juxtapositions between their analogous blade and handle portions. Including the transition portion 26 as described permits all surfaces which may contact a patient's teeth to simply slide thereover, without any abrupt impact as the instrument advances and retreats along its intended pathway of movement during an intubation.

Lobe 16 (a "tissue elevation lobe member") and its position relative to the remaining portions or components of Laryngoscope 10 represents the single most important feature of the present invention, with respect to effecting its optimal, beneficial use. Lobe 16 may be formed as a structure which is of a partial spherical shape, a substantially cylindrical shape (lying transverse to the aforementioned Line B), or some variation of either. In any event, lobe 16 represents an enlargement at or near the distal most terminus of Laryngoscope 10 and is useful in lifting, or elevating a patient's tongue and surrounding tissues to more easily visualize the vocal chords during an intubation. Unlike conventional Laryngoscopes, Laryngoscope 10 effects a greater degree of tissue displacement, relative to movement of the handle portion 12 and blade portion 14, such that one working in "tight spaces" anatomy can achieve optimal visualization results, despite minimum latitude for manipulating the instrument.

The contouring and relative geometry of lobe 16 can vary, but the preferred embodiment presently includes a lobe which is sized, shaped and relatively situated such that a Line C which passes through the distal most extend of the lobe 16 and substantially through the center point of light window 24 will, where such lines would intersect, intersect line A at an approximately 50° angle and Line B at an approximately 20° angle (not shown in the drawing). This configuration can be achieved in several different ways, but, in the preferred embodiment, is achieved through a combination of the orientation of lobe extension 22, relative to blade segment 20, and the size and shape of lobe 16 itself.

It should be understood that lobe 16 is to be a distinct, separately identifiable portion of Laryngoscope 10 in general, and of blade portion 14 in particular. In order for lobe 16 to optimally perform its intended function, it must "reach" beyond and above that which supports it to lift the contacted tissues relative to the over-all orientation of blade portion 14. Therefore, this design feature is fundamentally different from a blade portion of a different Laryngoscope design which is substantially uniform, or mildly tapered along its length and/or is in some manner non-linear over-all.

The product of this configuration is that a patient's tongue is, immediately upon insertion of Laryngoscope 10, displaced to a degree which, when using Laryngoscope 10, is equivalent to a conventional Laryngoscope having already been rotated about a rotational axis by approximately 20°. This translates into a "bonus" of 20° or rotation that the medical or surgical professional still has available to achieve the ultimately desired results.

The combination of the relative orientations of handle portion 12 and blade portion 14, and of lobe 16 produced an Laryngoscope which meets and exceeds all of the stated objects. It is believed that the ease with which heretofore even difficult intubations will be possible (or, at least, made easier), Laryngoscope 10 will find effective use, not only in hospital environments, but in field operations through use by lesser-trained and experienced personnel, such as medics and EMS technicians. This, quite literally, translates into saved lives.

The material from which Laryngoscope 10 is suggested to be constructed, not only facilitates the economical addition of the lighting features as described above, but also renders it suitable for "disposable" use. Again, this aspect of the device will result in its proliferation in the non-hospital environments where lives, otherwise lost for lack of a more user-friendly Laryngoscope, will be saved instead.

Although the invention has been described with reference to specific embodiments, this description should not be construed in a limited sense. Various modifications of the disclosed embodiments, as well as alternative embodiments of the inventions, will become apparent to persons skilled in the art upon the reference to the description of the invention.

It is, therefore, contemplated that the appended claims will cover such modifications that fall within the scope of the invention. It should be particularly understood that the relative angles discussed above are approximations, and relative changes between the angles and/or individual geometric changes will fall within the scope of the present invention, if such still performs the stated functions in the substantially in the manner described.

We claim:
1. A Laryngoscope comprising:
a body member having a handle portion, a blade portion and an arcuate transitional portion, which said arcuate transitional portion lies between said handle portion and said blade portion;
wherein said handle portion extends in a first direction substantially along a handle portion axis in a Laryngoscope reference plane,
wherein said blade portion consists of a blade segment and a lobe extension, wherein said blade segment extends in a second direction substantially along a blade portion axis in said Laryngoscope reference plane;
wherein said handle portion axis and said blade portion axis meet at an approximately 70 degree angle within said Laryngoscope reference plane;
wherein said arcuate transitional portion is configured to extend along a curved path between a distal end of said handle portion and a proximal end of said blade portion; and
wherein said arcuate transitional portion is designed to protect a patient's teeth when said Laryngoscope is pivoted in said laryngoscope reference plane;
a tissue displacement lobe extending from a distal end of said lobe extension, said tissue displacement lobe being of a partial spherical or a substantially cylindrical shape, lying transverse in relation to said handle portion axis, said tissue displacement lobe designed to displace tissue during negotiation of anatomical structures, said negotiation encountered while pivoting said Laryngoscope in said Laryngoscope reference plane to optimize visualization of vocal cords and to avoid damage to said anatomical structures of an oropharyngx; and
wherein said tissue displacement lobe is sized and shaped whereby a line, lying within said Laryngoscope reference plane and passing between a distal end of said tissue displacement lobe and substantially a center point of a light window defines an approximately 50 degree angular deviation from said blade portion axis within said Laryngoscope reference plane, with said line accordingly defining within said Laryngoscope reference plane, respectively, an approximately 20 degree angle relative to said handle portion axis.

2. The Laryngoscope of claim 1 wherein said body member is configured of a light-transmitting plastic material and wherein said blade segment and said lobe extension are respectively configured whereby a substantially angular stepdown is formed at a transition region between the distal end of said blade segment and a proximal end of said lobe extension, whereby a portion of light transmitted into said body member substantially from a distal end of said handle portion projects from said substantially angular stepdown.

* * * * *